United States Patent
Kiniwa et al.

(10) Patent No.: US 10,264,236 B2
(45) Date of Patent: Apr. 16, 2019

(54) CAMERA DEVICE

(71) Applicant: PANASONIC INTELLECTUAL PROPERTY MANAGEMENT CO., LTD., Osaka (JP)

(72) Inventors: Yuji Kiniwa, Fukuoka (JP); Haruo Kogane, Fukuoka (JP); Emi Matsumoto, Fukuoka (JP); Kenji Kobayashi, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 85 days.

(21) Appl. No.: 15/440,560

(22) Filed: Feb. 23, 2017

(65) Prior Publication Data

US 2017/0251196 A1   Aug. 31, 2017

(30) Foreign Application Priority Data

Feb. 29, 2016   (JP) .................................. 2016-038228

(51) Int. Cl.
*H04N 13/214* (2018.01)
*H04N 13/218* (2018.01)
(Continued)

(52) U.S. Cl.
CPC ............ *H04N 13/225* (2018.05); *A61B 1/04* (2013.01); *A61B 90/20* (2016.02); *A61B 90/361* (2016.02); *H04N 5/2256* (2013.01); *H04N 5/23232* (2013.01); *H04N 5/23245* (2013.01); *H04N 7/10* (2013.01); *H04N 13/218* (2018.05); *H04N 13/257* (2018.05); *H04N 13/289* (2018.05); *H04N 13/296* (2018.05);
(Continued)

(58) Field of Classification Search
None
See application file for complete search history.

(56) References Cited

U.S. PATENT DOCUMENTS

2014/0350338 A1*  11/2014  Tanaka ............... A61B 1/00009
                                                   600/111
2016/0029011 A1    1/2016  Mizoguchi et al.
(Continued)

FOREIGN PATENT DOCUMENTS

JP          8-248328        9/1996
JP          9-327042        12/1997
(Continued)

*Primary Examiner* — Chikaodili E Anyikire
(74) *Attorney, Agent, or Firm* — Greenblum & Bernstein, P.L.C.

(57) ABSTRACT

A camera device includes a camera head that captures an observation image of a target site which is obtained by a surgical microscope, and a camera control unit that processes a signal of the observation video captured by the camera head. The camera head captures right and left observation images having a parallax from the surgical microscope to obtain a high-resolution observation video including right and left parallax videos for one screen, and the camera control unit cuts out the right parallax video and the left parallax video from the observation video including the right and left parallax videos to generate a high-resolution 3D video which is displayed on a monitor in 3D and with which stereoscopic observation can be performed.

14 Claims, 12 Drawing Sheets

(51) Int. Cl.
  *H04N 13/225* (2018.01)
  *A61B 90/20* (2016.01)
  *H04N 13/257* (2018.01)
  *H04N 13/296* (2018.01)
  *H04N 13/289* (2018.01)
  *A61B 1/04* (2006.01)
  *H04N 5/232* (2006.01)
  *H04N 7/10* (2006.01)
  *H04N 5/225* (2006.01)
  *A61B 90/00* (2016.01)
  *A61B 1/00* (2006.01)
  *H04N 13/30* (2018.01)

(52) U.S. Cl.
  CPC ... *A61B 1/00193* (2013.01); *A61B 2090/3616* (2016.02); *A61B 2090/3618* (2016.02); *H04N 7/104* (2013.01); *H04N 13/30* (2018.05); *H04N 2005/2255* (2013.01); *H04N 2213/001* (2013.01)

(56) References Cited

U.S. PATENT DOCUMENTS

2016/0261846 A1  9/2016  Kasumi et al.
2017/0046842 A1* 2/2017  Yamaguchi ........ A61B 1/00009

FOREIGN PATENT DOCUMENTS

| JP | 10-004567 | 1/1998 |
| JP | 2006-284989 | 10/2006 |
| JP | 2011-206425 | 10/2011 |
| WO | 2014/163109 A1 | 10/2014 |
| WO | 2015/083451 A1 | 6/2015 |

\* cited by examiner

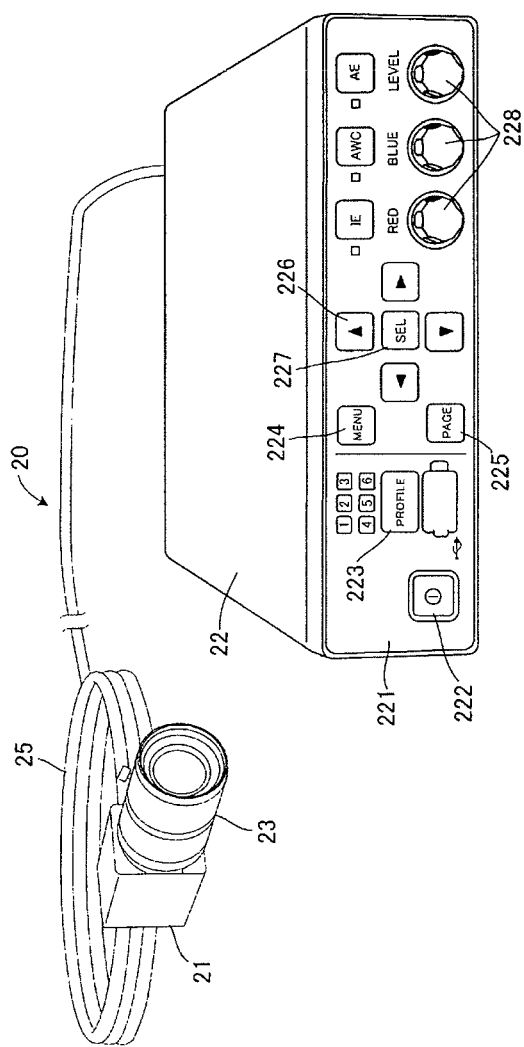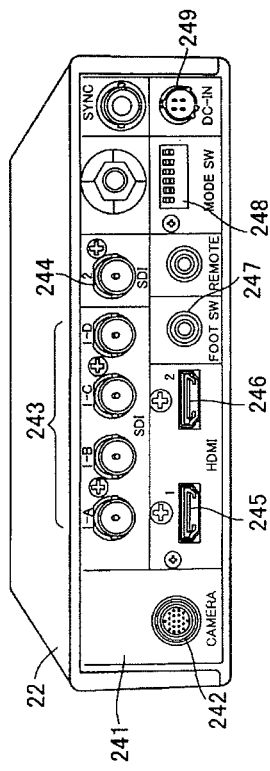
FIG. 3A
FIG. 3B

CAMERA DEVICE

BACKGROUND

1. Technical Field

The present disclosure relates to a camera device such as a surgical microscope system used in the medical field.

2. Description of the Related Art

A camera device, which captures an observation image and displays the observation image on a monitor, is used for, for example, microsurgery which a surgeon performs while observing a fine surgical site by using a microscope or endoscopic surgery which a surgeon performs while observing a surgical site inside a patient's body by using an endoscope. With a medical camera system which includes such a camera device, it is possible to visually recognize a target site with ease and in detail by using a large observation image displayed on the monitor. In addition, a plurality of persons related to surgery can observe the surgical site and an image of the surgical site can be shared.

As the related art of such a camera device, there is a stereoscopic endoscope device disclosed in Japanese Patent Unexamined Publication No. 2011-206425, for example. In Japanese Patent Unexamined Publication No. 2011-206425, a wide angle image (a 2D image), a stereo vision image (a 3D image), and an image for navigation (an entire region image) are obtained by using an endoscope and a display area of the 3D image is controlled such that the 3D image is displayed on a portion of a 2D image. Accordingly, fatigue or tension of a person referring to the images is alleviated.

In a medical camera system, for clear observation of a target site on which surgery, treatment or the like is performed, it is desirable that the resolution of a displayed image is as high as possible. In addition, since it is possible to accurately and easily grasp the distance and the size of an observation target through stereoscopic observation of the target site, the demand for a 3D video that provides a stereoscopic observation video to an observer has been increased. Particularly, for surgery on a fine structure, a high-resolution 3D image is needed. The camera device in the related art has a problem that it is not possible to visually clearly recognize the observation video in detail or the like. In addition, in order to generate a high-resolution 3D video which is required in the medical field, it is necessary to use two cameras to capture right and left parallax videos.

SUMMARY

An object of this disclosure is to provide a camera device that is capable of capturing and outputting a high-resolution 3D video, which is required in the medical field, with one camera in order to solve the abode-described problem of the related art.

The disclosure provides a camera device which is connected to a medical optical instrument. The camera device includes a camera head that captures an observation image of a target site which is obtained by the medical optical instrument, and a camera control unit that is connected to the camera head and processes a signal of the observation video captured by the camera head. The camera head captures right and left observation images having a parallax from the medical optical instrument to obtain a high-resolution observation video including right and left parallax videos for one screen, and the camera control unit cuts out the right parallax video and the left parallax video from the observation video including the right and left parallax videos to generate a high-resolution 3D video which is displayed on a monitor in 3D and with which stereoscopic observation can be performed.

According to the disclosure, there is provided a camera device that can capture and output a high-resolution 3D video, which is required in the medical field, with one camera.

BRIEF DESCRIPTION OF THE DRAWINGS

FIG. 3A is a view illustrating a camera head and a CCU of the camera device according to the embodiment;

FIG. 3B is a view illustrating a rear surface of the CCU of the camera device according to the embodiment;

DETAILED DESCRIPTION

Hereinafter, a specific embodiment (hereinafter, referred to as "the embodiment") of a camera device of the disclosure will be described in detail with reference to the drawings. However, excessively detailed description will be omitted in some cases. For example, detailed description of known matters or duplicated description of substantially the same matters will be omitted in some cases. This is to prevent the following description from being unnecessarily redundant and to help a person skilled in the art to easily understand the disclosure. Attached drawings and the following description are provided to help a person skilled in the art to sufficiently understand the disclosure and are not intended to limit the claimed subject matter.

In addition, in the embodiment which will be described below, a configuration example of a medical camera system which includes a camera device according to the embodiment will be described. As a specific application example of the embodiment, a configuration of a camera device in a surgical microscope system will be described. Embodiments of the camera device according to the disclosure are not limited to the contents of the following embodiment.

The camera device of the embodiment is capable of capturing and outputting a high-resolution observation video, for example, an observation video of which the resolution is a 4K resolution (2160p or the like) (hereinafter, referred to as a "2D video") and an observation video of which the resolution is a full high vision (FHD: Full High Definition) resolution (1080p or the like) (hereinafter, referred to as a "3D video") and with which stereoscopic observation can be performed. The full high vision (FHD) resolution may be referred to as a 2K resolution.

System Configuration 1

Figure 1:
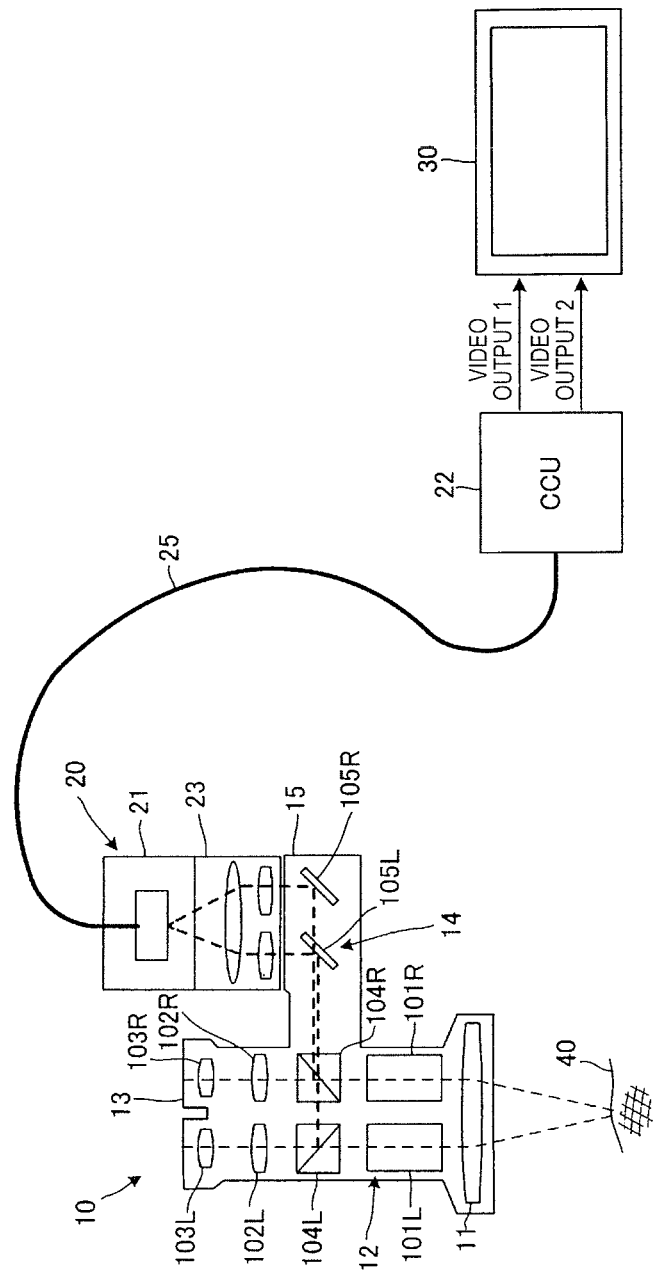
FIG. 1 is a system configuration diagram which illustrates a surgical microscope system to which a medical camera system including a camera device according to an embodiment is applied.

FIG. 1 is a system configuration diagram which illustrates a surgical microscope system to which a medical camera system including the camera device according to an embodiment is applied. The surgical microscope system includes surgical microscope 10, camera device 20, and monitor 30, which are examples of medical optical instruments. Camera device 20 includes camera head 21 that captures an observation image of a target site which is obtained by surgical microscope 10 and camera control unit (CCU) 22 that controls camera head 21 to process a signal of the captured observation video. Camera head 21 and CCU 22 are connected to each other via signal cable 25. Camera head 21 is mounted on and connected to camera mounting portion 15 of surgical microscope 10. An output terminal of CCU 22 is connected to monitor 30 which displays the observation video.

Surgical microscope 10 is a binocular microscope and includes object lens 11, two observation optical systems 12 which respectively correspond to right and left eyes of an observer, eye piece portion 13, camera image capturing optical system 14, and camera mounting portion 15. Observation optical systems 12 include zoom optical systems 101R and 101L, image forming lenses 102R and 102L, and eyepiece lenses 103R and 103L. Two observation optical systems 12 are disposed with an optical axis of object lens 11 interposed therebetween. In observation optical systems 12, a right-eye observation image and a left-eye observation image that are enlarged at a predetermined magnification by zoom optical systems 101R and 101L are formed on image forming lenses 102R and 102L and the right and left observation images having a parallax are guided to eye piece portion 13 through eyepiece lenses 103R and 103L. When the observer looks into eye piece portion 13 with both eyes, the observer can visually recognize subject 40 which is a target site in a stereoscopic manner.

Camera image capturing optical system 14 includes beam splitters 104R and 104L and mirrors 105R and 105L. Camera image capturing optical system 14 deflects and separates light of the right and left observation images passing through observation optical systems 12 by using beam splitters 104R and 104L and reflects the light by using mirrors 105R and 105L to guide the right and left observation images having a parallax toward camera mounting portion 15. When image capturing is performed with camera head 21 of camera device 20 mounted on camera mounting portion 15, an observation video for a 3D display operation, with which the stereoscopic observation can be performed, can be obtained.

Figure 2:
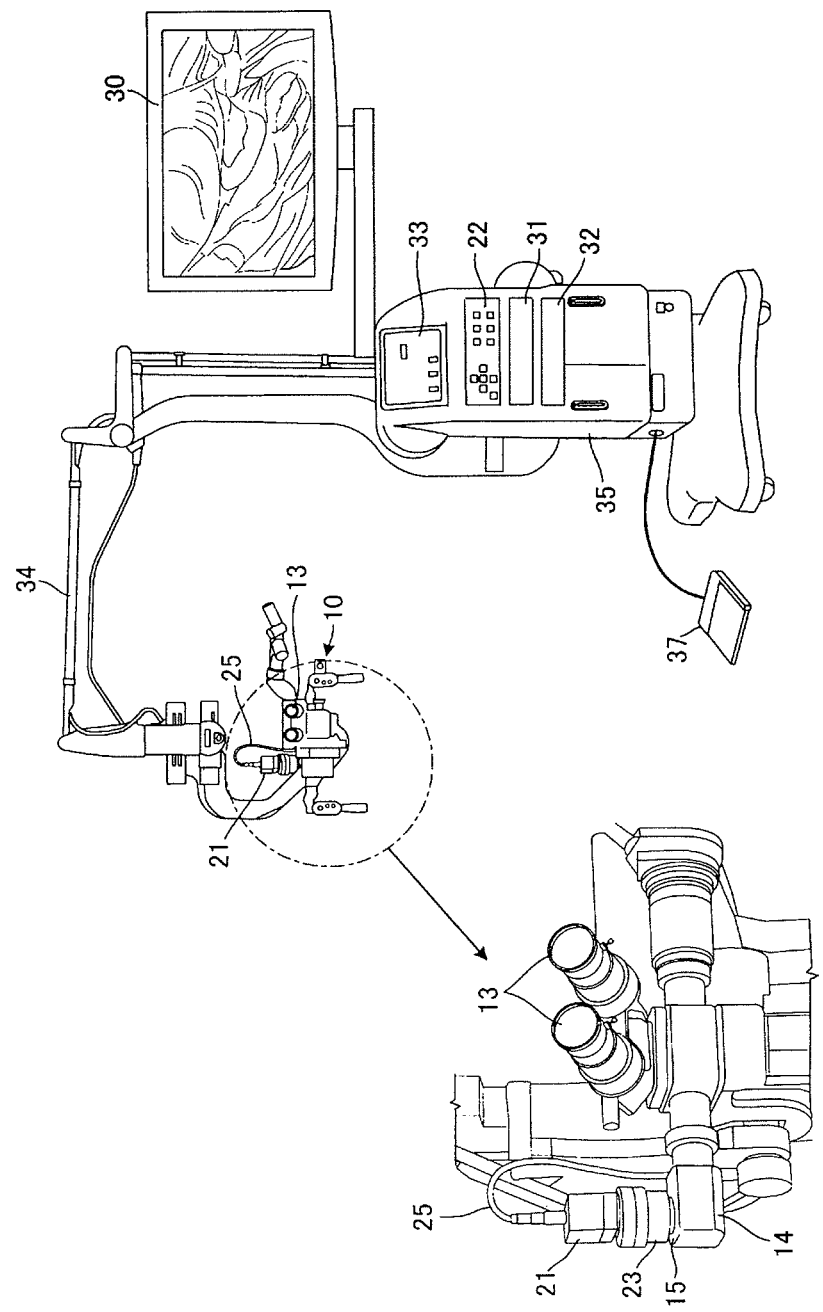
FIG. 2 is a view illustrating the appearance of the surgical microscope system according to the embodiment.

FIG. 2 is a view illustrating the appearance of the surgical microscope system according to the embodiment. In surgical microscope 10, eye piece portion 13 is provided on an upper portion of a microscope main body, a housing of camera image capturing optical system 14 laterally extends from a base end portion of eye piece portion 13, and camera mounting portion 15 is provided. Camera mounting portion 15 opens upward and is formed such that image capturing lens unit 23 of camera head 21 can be mounted thereon. Image capturing lens unit 23 is detachable with respect to a main body of camera head 21 and is replaceable. Image capturing lens unit 23 is configured such that image capturing optical systems with different optical properties can be selectively used depending on the purpose. Camera head 21 is constituted by a three-CCD image capturing unit that includes a light splitting prism which splits a subject image into RGB components and three image sensors which capture a red subject image, a green subject image, and a blue subject image, respectively. Note that, a single CCD image capturing unit which includes one image sensor may also be used.

The surgical microscope system includes light source device 31 which illuminates the target site, recorder 32 which records the observation video that is captured by camera device 20, operation unit 33 for operating the surgical microscope system, and foot switch 37 with which the observer inputs the operation by using a foot. Operation unit 33, CCU 22, light source device 31, and recorder 32 are accommodated in control unit housing 35. Monitor 30 is disposed in the vicinity of control unit housing 35. Surgical microscope 10 is attached to displaceable supporting arm 34 and is connected to control unit housing 35 via supporting arm 34.

Configuration of Camera Device

FIGS. 3A and 3B are views illustrating the appearance of the camera device according to the embodiment, where FIG. 3A is a view illustrating the camera head and the CCU and FIG. 3B is a view illustrating a rear surface of the CCU. Camera head 21 is connected to a rear surface of a housing of CCU 22 via signal cable 25. Camera head 21 captures a high-resolution observation video and is configured such that camera head 21 can capture an observation video including right and left parallax videos for one screen by using the three-CCD or single CCD image capturing unit in a case of capturing a 3D video.

Front panel 221 of CCU 22 is provided with power switch 222, profile selection switch 223, menu switch 224, page switching switch 225, vertical and lateral movement switches 226, selection switch 227, and image quality adjustment switch 228. In addition, rear panel 241 of CCU 22 is provided with camera terminal 242, serial digital interface (SDI) video output terminals 243 and 244, high-definition multimedia interface (HDMI) (registered trademark) video output terminals 245 and 246, foot switch terminal 247, mode switch 248, and DC power input terminal 249.

CCU 22 is capable of selectively outputting a 4K resolution 2D video (4K 2D video) and an FHD resolution 3D video (an FHD 3D video) while switching between operation modes. Profile selection switch 223 is a switch for selecting a preset profile in which the operation mode of CCU 22 is set. Switching between an operation mode for the 4K 2D video and an operation mode for the FHD 3D video can be performed by selecting a profile with profile selection switch 223, by selecting an operation mode with menu switch 224 and selection switch 227, by setting an operation mode with mode switch 248 on the rear surface, or the like.

SDI video output terminals 243 and 244 respectively correspond to two types of output terminals of CH1 and CH2 conforming to the 3G-SDI standard. The number of SDI video output terminals 243 of CH1 is four and SDI video output terminals 243 can output both of the 4K video and the FHD video. SDI video output terminal 244 of CH2 can output the FHD video. HDMI (registered trademark) (the same applies hereinafter) video output terminals 245 and 246 correspond to two types of output terminals of CH1 and CH2. HDMI video output terminal 245 of CH1 conforms to the HDMI 2.0 standard and can output both of the 4K video and the FHD video. HDMI video output terminal 246 of CH2 conforms to the HDMI 1.4 standard and can output the FHD video. Regarding the video output terminals, both of the two types of output terminals may be configured to be capable of outputting both of the 4K video and the FHD video. In addition, the shapes and the number of the video output terminals are not limited to those described in the drawings and the disclosure also can be applied to a case where the video output terminals conform to another standard.

Signal cable 25 of camera head 21 is connected to camera terminal 242. Monitor 30 is connected to at least one of SDI video output terminals 243 and 244 and HDMI video output terminals 245 and 246 via a video signal cable (not shown). A power supply device which supplies DC power via a power cable (not shown) is connected to DC power input terminal 249. Foot switch 37 is connected to foot switch terminal 247.

Figure 4:
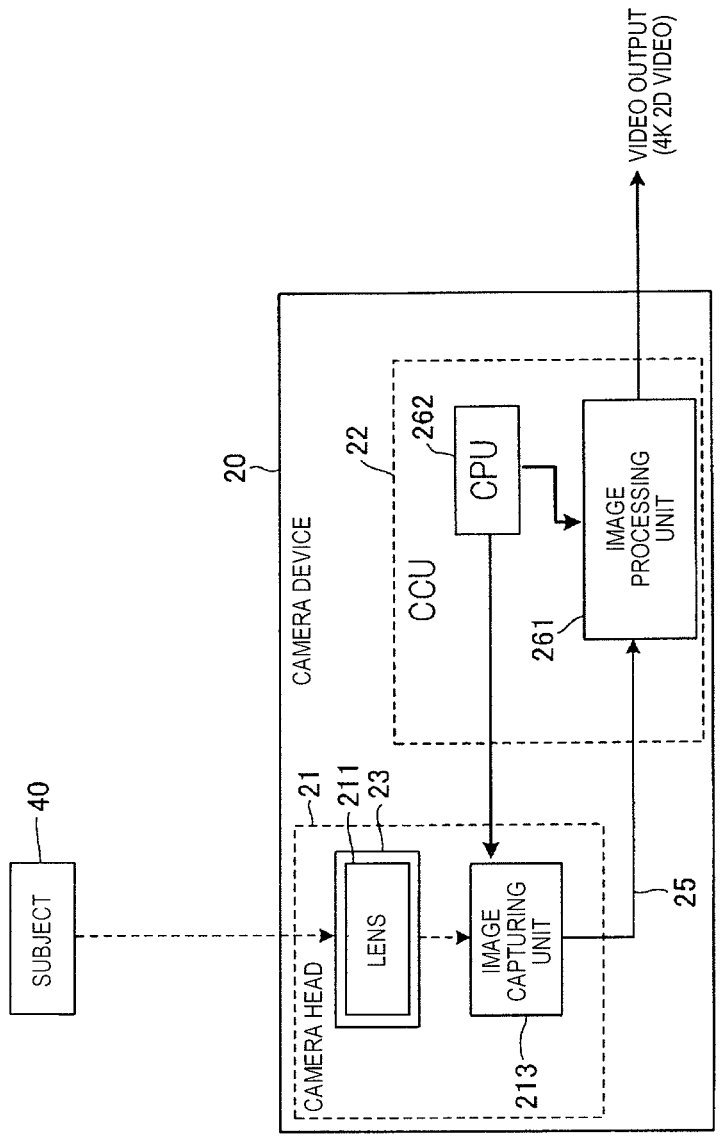
FIG. 4 is a block diagram illustrating a functional configuration of the camera device according to the embodiment at the time of a 2D video capturing operation.

FIG. 4 is a block diagram illustrating a functional configuration of the camera device according to the embodiment at the time of a 2D video capturing operation. In a case of capturing a 4K resolution 2D video by using camera device 20, camera head 21 is used being attached to camera mounting portion 15 of surgical microscope 10 in a state where monocular lens 211 on which the subject image is formed is mounted in image capturing lens unit 23 of camera head 21. Light from subject 40 passes through lens 211 and forms an image on each of image capturing surfaces of the three image sensors of three-CCD image capturing unit 213 so that subject images of RGB colors are captured. That is, camera head 21 includes image capturing unit 213 which captures the observation image from surgical microscope 10 and obtains a high-resolution (here, FHD (2K) resolution) observation video. Image capturing unit 213 can obtain a high-resolution captured video and is constituted by a three-CCD FHD image sensor which can capture an FHD resolution video for each of RGB colors. The FHD image sensor is constituted by image capturing elements such as a charged-coupled device (CCD) and a complementary metal oxide semiconductor (CMOS). In a case where a single CCD image capturing unit is used, the image capturing unit may be constituted by a 4K image sensor, which can capture a 4K resolution video, and a color filter. A video signal of a captured video of the subject which is captured by camera head 21 is transmitted to CCU 22 via signal cable 25.

CCU 22 includes image processor 261, which includes a signal processing circuit that processes a signal of a video captured by camera head 21, and central processing unit (CPU) 262, which is an example of processors constituting a control unit (computer) that sets the operation mode of image processor 261 and image capturing unit 213 and controls each operation. Image processor 261 is configured by using, for example, a field-programmable gate array (FPGA) such that setting and changing of the circuit structure and the operation can be performed using a program. Image processor 261 generates a high-resolution (here, 4K resolution) 2D video (4K 2D video) from 2K videos R, G, and B (videos R, G, and B for 4K), which are transmitted from camera head 21 and respectively correspond to RGB colors, and outputs the high-resolution 2D video to monitor 30 as a video output.

Figure 5:
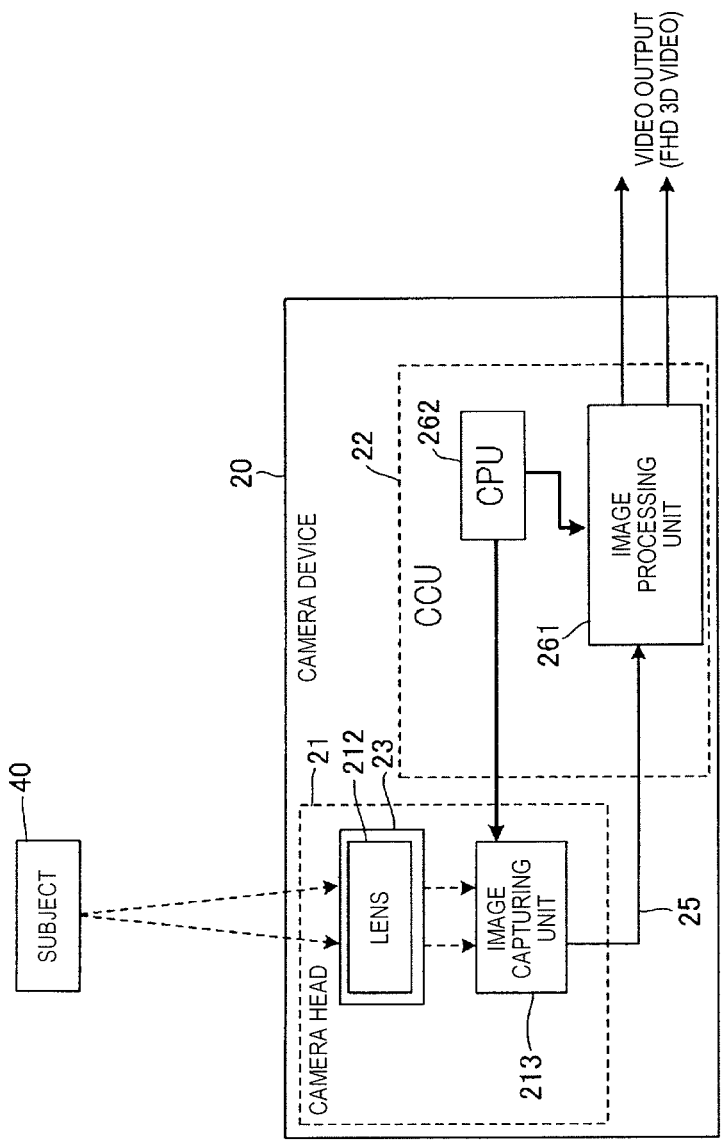
FIG. 5 is a block diagram illustrating a functional configuration of the camera device according to the embodiment at the time of a 3D video capturing operation.

FIG. 5 is a block diagram illustrating a functional configuration of the camera device according to the embodiment at the time of a 3D video capturing operation. In a case of capturing the FHD resolution 3D video by using camera device 20, camera head 21 is used being attached to camera mounting portion 15 of surgical microscope 10 in a state where binocular lens 212 on which right and left subject images having a parallax are formed is mounted in image capturing lens unit 23 of camera head 21. Right and left videos of the subject having a parallax may also be captured using a monocular lens. Light from subject 40 passes through lens 212 and forms laterally adjacent two (right and left) images having a parallax on each of image capturing surfaces of the three image sensors of three-CCD image capturing unit 213 so that right and left subject images of RGB for a 3D video are captured. That is, camera head 21 includes image capturing unit 213 which captures right and left observation images having a parallax from surgical microscope 10 and obtains a high-resolution (here, FHD (2K) resolution) observation video including right and left parallax videos for one screen. A video signal for a 3D video of the subject which is captured by camera head 21 is transmitted to CCU 22 via signal cable 25.

Instead of replacing a lens for 2D in image capturing lens unit 23 with a lens for 3D in a case of capturing a 3D video using camera head 21, an adapter may be provided in camera mounting portion 15 of surgical microscope 10 and an optical system for 2D in the adapter may be replaced with an optical system for 3D. Alternatively, the medical optical instrument itself such as surgical microscope 10 which is connected to camera head 21 may be configured to be replaceable so that a device with an observation optical system for 2D is mounted when capturing a 2D video and a device with an observation optical system for 3D is mounted when capturing a 3D video.

Image processor 261 of CCU 22 generates a high-resolution (here, FHD resolution) 3D video (FHD 3D video) from right and left 2K videos R, G, and B for a 3D display operation (2K videos R, G, and B for the right side of the 3D video and 2K videos R, G, and B for the left side of the 3D video), which are transmitted from camera head 21 and respectively correspond to RGB colors, and outputs the high-resolution 3D video to monitor 30 as two (right and left) video outputs 1 and 2 for the 3D display operation. A configuration and operation of image processor 261 which generates the 4K 2D video or the FHD 3D video will be described later. In a case where the stereoscopic observation of the observation video is performed, a 3D video is displayed on monitor 30 in such a manner that the observer can observe a left parallax video and a right parallax video with the observer's respective eyes by using monitor 30 alone or using 3D glasses worn by the observer also.

Figure 6:
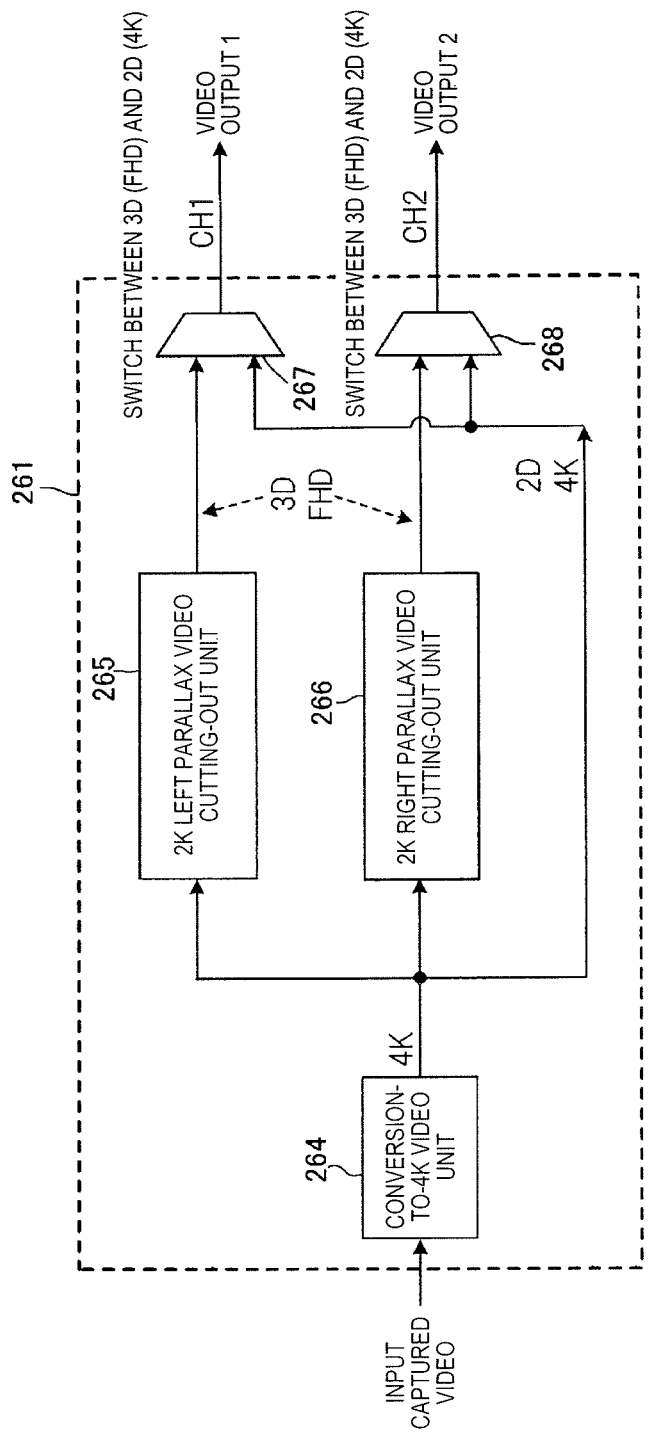
FIG. 6 is a block diagram illustrating a first example of a functional configuration of an image processor in the camera device according to the embodiment.

FIG. 6 is a block diagram illustrating a first example of a functional configuration of the image processor in the camera device according to the embodiment. Image processor 261 includes 4K video producing unit 264, 2K left parallax video cutting-out unit 265, 2K right parallax video cutting-out unit 266, and video output switching units 267 and 268. 4K video producing unit 264 receives 2K videos R, G, and B, which are captured by three-CCD camera head 21 and respectively correspond to RGB colors, and generates a 4K resolution video as a resolution enhancement process for the captured video. As a method for producing a 4K video, for example, a known "pixel shifting" process is used. 4K video producing unit 264 performs a process of shifting pixels of 2K video R and 2K video B by a ½ pixel distance in the vertical direction and the horizontal direction with respect to pixels of 2K video G and generates a 4K resolution color video. In a case of capturing a 4K resolution 2D video, a 4K 2D color video is generated from 2K videos R, G, and B for a 2D display operation. In a case of capturing an FHD resolution 3D video, a 4K video (a 3D right parallax video and a 3D left parallax video) including right and left FHD resolution parallax videos is generated from 2K videos R, G, and B for the right side and the left side for the 3D display operation, which are captured by laterally adjacent image sensors. In a case where a single CCD image capturing unit is used, 4K video producing unit 264 is not provided in image processor 261 and a signal of a 4K resolution color video which is captured by camera head 21 is processed being input to image processor 261.

2K left parallax video cutting-out unit 265 cuts out a 2K left parallax video, which corresponds to a region for the left side and is a half of the 4K video including the FHD resolution right and left parallax videos output from 4K video producing unit 264, from the 4K video and generates an FHD video for the left side for the 3D display operation (the 3D left parallax video).

2K right parallax video cutting-out unit 266 cuts out a 2K right parallax video, which corresponds to a region for the right side and is the other half of the 4K video including the FHD resolution right and left parallax videos output from 4K video producing unit 264, from the 4K video and generates an FHD video for the right side for the 3D display operation (the 3D right parallax video).

Video output switching units 267 and 268 switch video signals to be output and output a video signal of the FHD resolution 3D video (3D (FHD)) or the 4K resolution 2D video (2D (4K)). In a case of outputting the FHD resolution 3D video (3D (FHD)), a video signal of the 3D left parallax video is output as video output 1 of channel CH1 and a video signal of the 3D right parallax video is output as video output 2 of channel CH2. In a case of outputting the 4K resolution 2D video (2D (4K)), a video signal may be output as both of video output 1 of channel CH1 and video output 2 of channel CH2 and the video signal may be output as only one of video output 1 of channel CH1 and video output 2 of channel CH2. In addition, the 4K resolution 2D video (2D (4K)) may be output via one of channel CH1 and channel CH2 and the FHD resolution 2D video (2D (FHD)) may be output via the other one of channel CH1 and channel CH2.

4K 2D Video Generating Process

Figure 7:
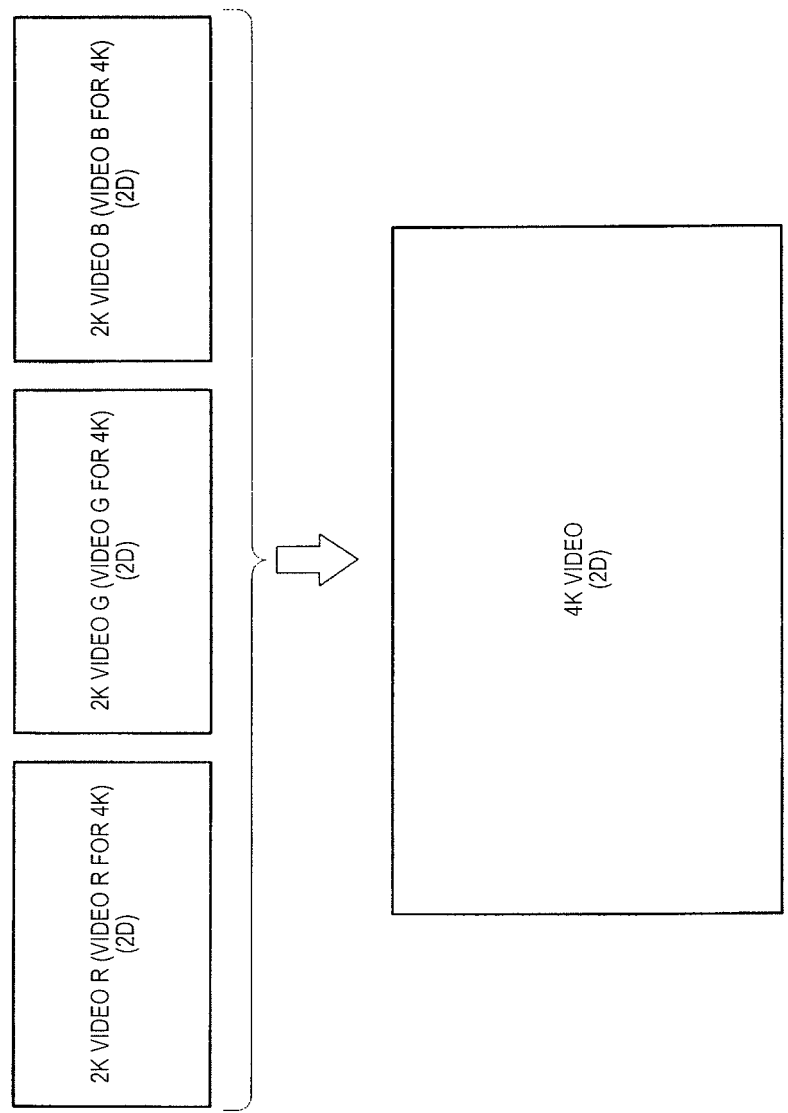
FIG. 7 is an explanatory diagram which illustrates an overview of a 2D video generating operation according to the embodiment.

FIG. 7 is an explanatory diagram which illustrates an overview of a 2D video generating operation according to the embodiment and schematically illustrates a process of generating the 4K resolution 2D video. In a case of capturing the 4K resolution 2D video by using camera device 20, 2K videos R, G, and B, which respectively correspond to RGB colors, are captured as 2D videos R, G, and B for 4K by three-CCD camera head 21. Next, 4K video producing unit 264 of image processor 261 produces a 4K video from 2K videos R, G, and B by performing the pixel shifting process with respect to video signals of 2K videos R, G, and B. In this manner, a 4K 2D color video is generated.

FHD 3D Video Generating Process

Figure 8:
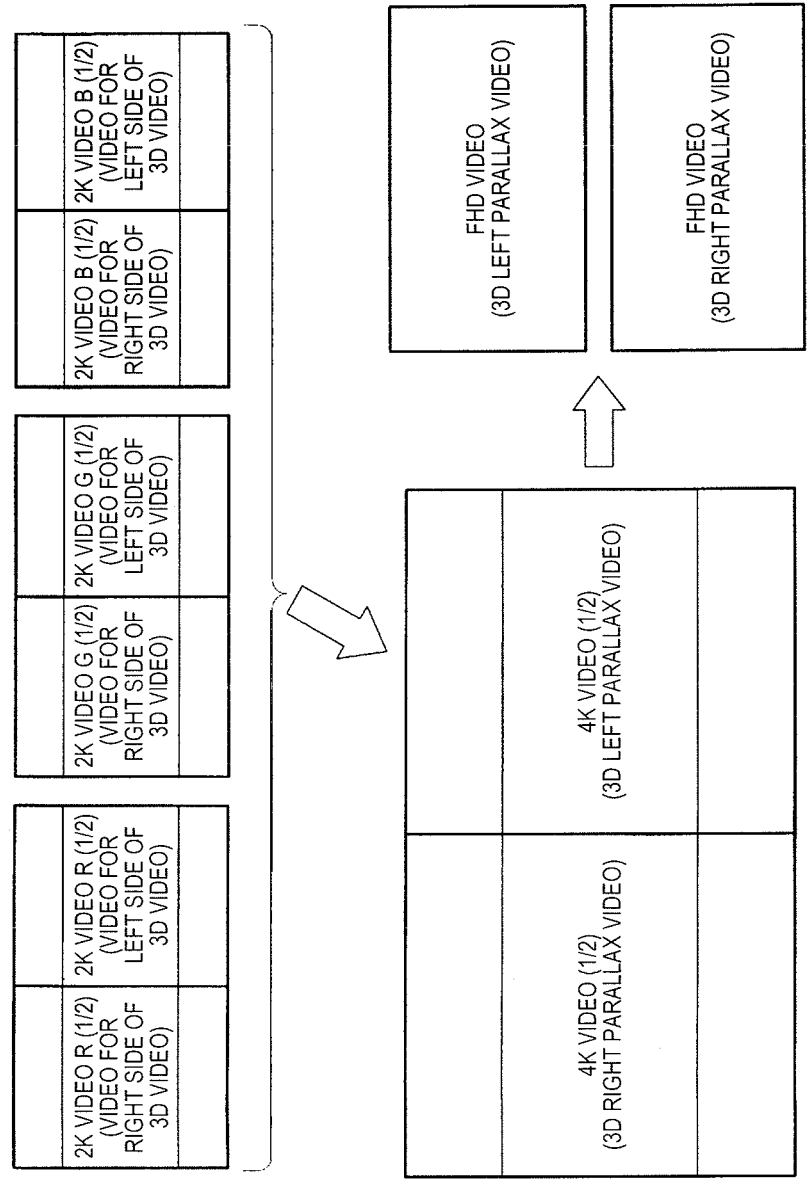
FIG. 8 is an explanatory diagram which illustrates an overview of a 3D video generating operation according to the embodiment.

FIG. 8 is an explanatory diagram which illustrates an overview of a 3D video generating operation according to the embodiment and schematically illustrates a process of generating the FHD resolution 3D video. In a case of capturing the FHD resolution 3D video by using camera device 20, three-CCD camera head 21 captures 2K videos R, G, and B for the right side and the left side for the 3D display operation (2K videos for the right side of the 3D video and 2 k videos for the left side of the 3D video), which respectively correspond to RGB colors, with laterally adjacent ½ regions of the image sensor. Next, 4K video producing unit 264 of image processor 261 produces a 4K video from 2K videos R, G, and B by performing the pixel shifting process with respect to video signals of 2K videos R, G, and B including right and left parallax videos. In this manner, a 4K color video (the 3D left parallax video and the 3D right parallax video) for the 3D display operation is generated. Subsequently, a process of cutting out the 2K left parallax video and the 2K right parallax video by respectively using 2K left parallax video cutting-out unit 265 and 2K right parallax video cutting-out unit 266 is performed to generate the FHD video (the 3D left parallax video and the 3D right parallax video) for the 3D display operation.

Figure 9:
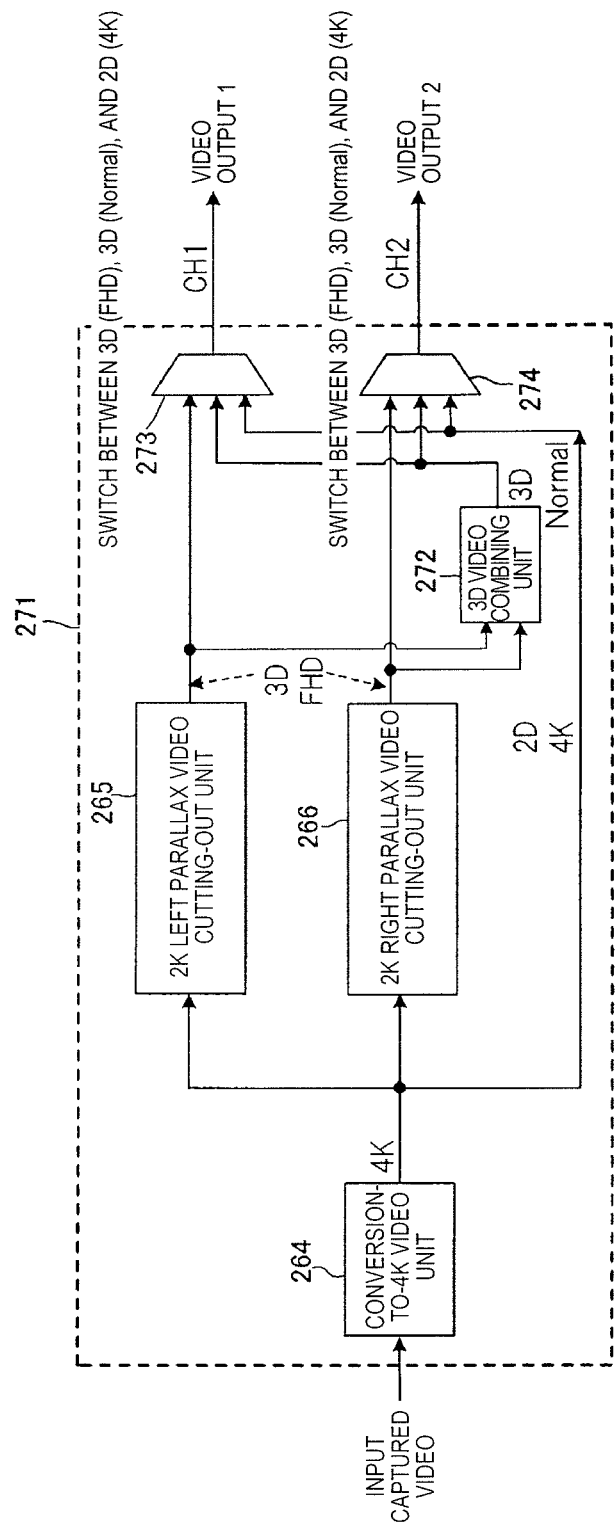
FIG. 9 is a block diagram illustrating a second example of a functional configuration of the image processor in the camera device according to the embodiment.

FIG. 9 is a block diagram illustrating a second example of a functional configuration of the image processor in the camera device according to the embodiment. As with the first example shown in FIG. 6, image processor 271 includes 4K video producing unit 264, 2K left parallax video cutting-out unit 265, and 2K right parallax video cutting-out unit 266. In addition, image processor 271 includes 3D video combining unit 272, and video output switching units 273 and 274. 3D video combining unit 272 performs a combining process of the 3D left parallax video output from 2K left parallax video cutting-out unit 265 and the 3D right parallax video output from 2K right parallax video cutting-out unit 266 to generate an HD resolution 3D video (3D (Normal)). For the 3D video combining process, a video conversion process (a 3D video producing process), which supports various 3D video transmission methods such as a side-by-side method in which a left parallax video and a right parallax video are disposed to be horizontally adjacent to each other and a line-by-line method in which a left parallax video and a right parallax video are disposed for each line, can be used.

Video output switching units 273 and 274 switch video signals to be output and output a video signal of the FHD resolution 3D video (3D (FHD)), the HD resolution 3D video (3D (Normal)), or the 4K resolution 2D video (2D (4K)). In a case of outputting the FHD resolution 3D video (3D (FHD)), a video signal of the 3D left parallax video is output as video output 1 of channel CH1 and a video signal of the 3D right parallax video is output as video output 2 of channel CH2. In a case of outputting the 4K resolution 2D video (2D (4K)) or the HD resolution 3D video (3D (Normal)), a video signal may be output as both of video output 1 of channel CH1 and video output 2 of channel CH2 and the video signal may be output as only one of video output 1 of channel CH1 and video output 2 of channel CH2.

Figure 10:
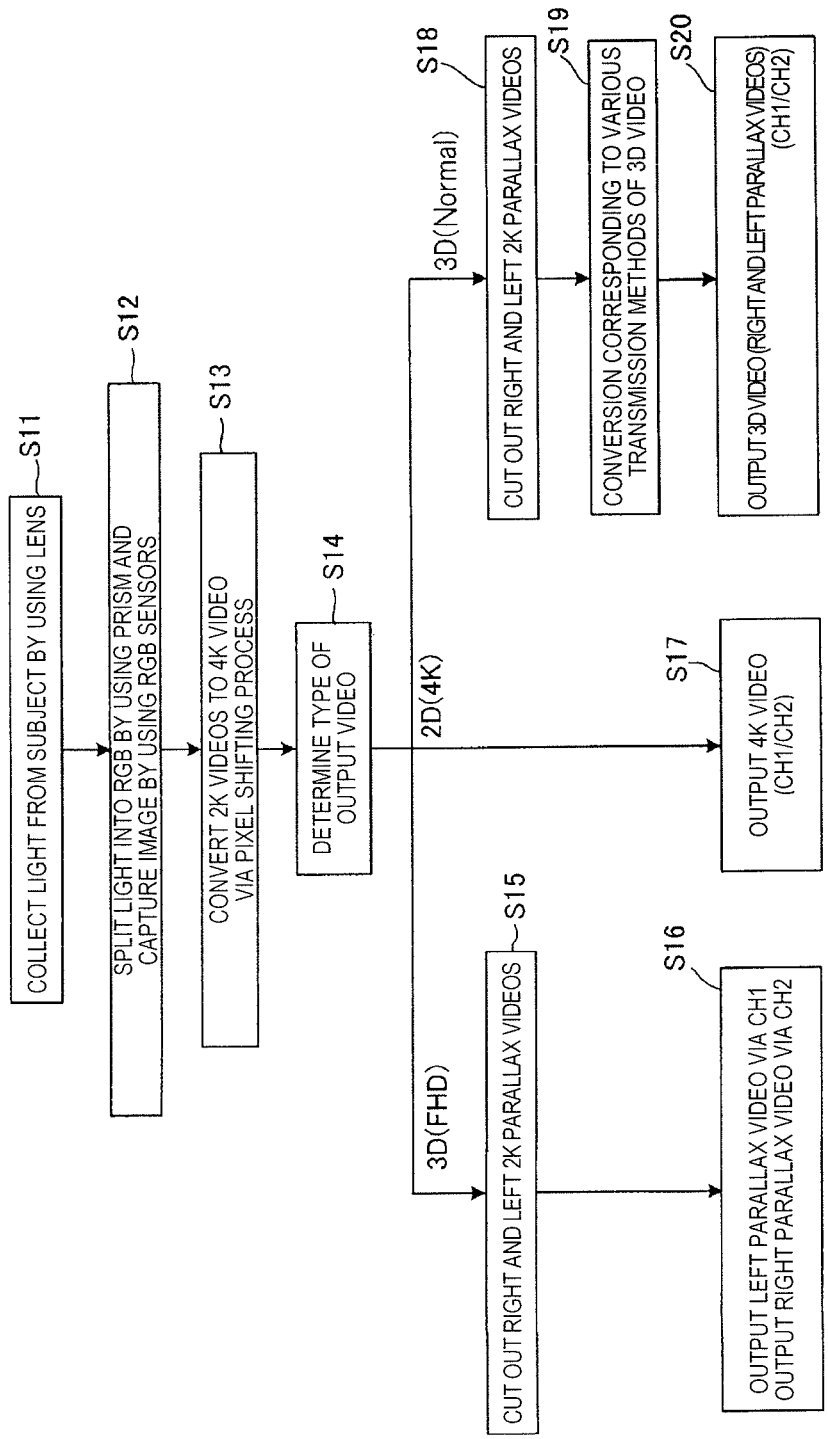
FIG. 10 is a flowchart for explaining an operation of the camera device according to the embodiment.

FIG. 10 is a flowchart for explaining an operation of the camera device according to the embodiment. Regarding camera device 20, light from subject 40, which is obtained by surgical microscope 10, is collected in camera head 21 by a lens of image capturing lens unit 23 (Step S11). In three-CCD image capturing unit 213 of camera head 21, a light splitting prism splits the light into subject images, which respectively corresponds to RGB colors, and the subject images are formed on each of image capturing surfaces of the three image sensors, which respectively corresponds to RGB colors. In this manner, a red FHD resolution subject image, a green FHD resolution subject image, and a blue FHD resolution subject image are captured (Step S12). Next, regarding camera device 20, in image processor 261 of CCU 22, a 4K video is produced from the captured 2K videos R, G, and B, which respectively correspond to RGB colors, through the pixel shifting process. In this manner, a 4K video is generated (Step S13). In addition, in CPU 262 of CCU 22, the type of the video to be output is determined and video outputs are switched while the operation of image processor 261 is set for each type of the FHD resolution 3D video (3D (FHD)), the 4K resolution 2D video (2D (4K)), and the HD resolution 3D video (3D (Normal))) (Step S14).

In a case of outputting the FHD resolution 3D video (3D (FHD)), in image processor 261, a process of cutting out two (right and left) 2K parallax videos (the 2K left parallax video and the 2K right parallax video) is performed (Step S15). In addition, in image processor 261, the 3D left parallax video is output via channel CH1 and the 3D right parallax video is output via channel CH2, as outputs for the FHD resolution 3D video for the 3D display operation (Step S16).

In a case of outputting the 4K resolution 2D video (2D (4K)), in image processor 261, a 4K video is output via both or any one of channel CH1 and channel CH2 as an output for the 4K resolution 2D video (Step S17).

In addition, in a case of outputting the HD resolution 3D video (3D (Normal)), in image processor 261, a process of cutting out two (right and left) 2K parallax videos (the 2K left parallax video and the 2K right parallax video) is performed (Step S18). Next, in image processor 261, the two (right and left) 2K parallax videos are combined and the video conversion process (the 3D video producing process) which supports various 3D video transmission methods is performed (Step S19). In addition, in image processor 261, 3D videos (right and left parallax videos) are output as outputs for the HD resolution 3D video (Step S20).

As described above, in System Configuration 1 of the embodiment, right and left parallax images, which are obtained by surgical microscope 10, are captured as an FHD resolution observation video including right and left parallax images in camera head 21 and an FHD resolution right parallax video and an FHD resolution left parallax video are generated and output in CCU 22. Therefore, an FHD resolution 3D video can be displayed on monitor 30. Accordingly, it is possible to capture a high-resolution 3D video for surgery which is required in the medical field.

System Configuration 2

Figure 11:
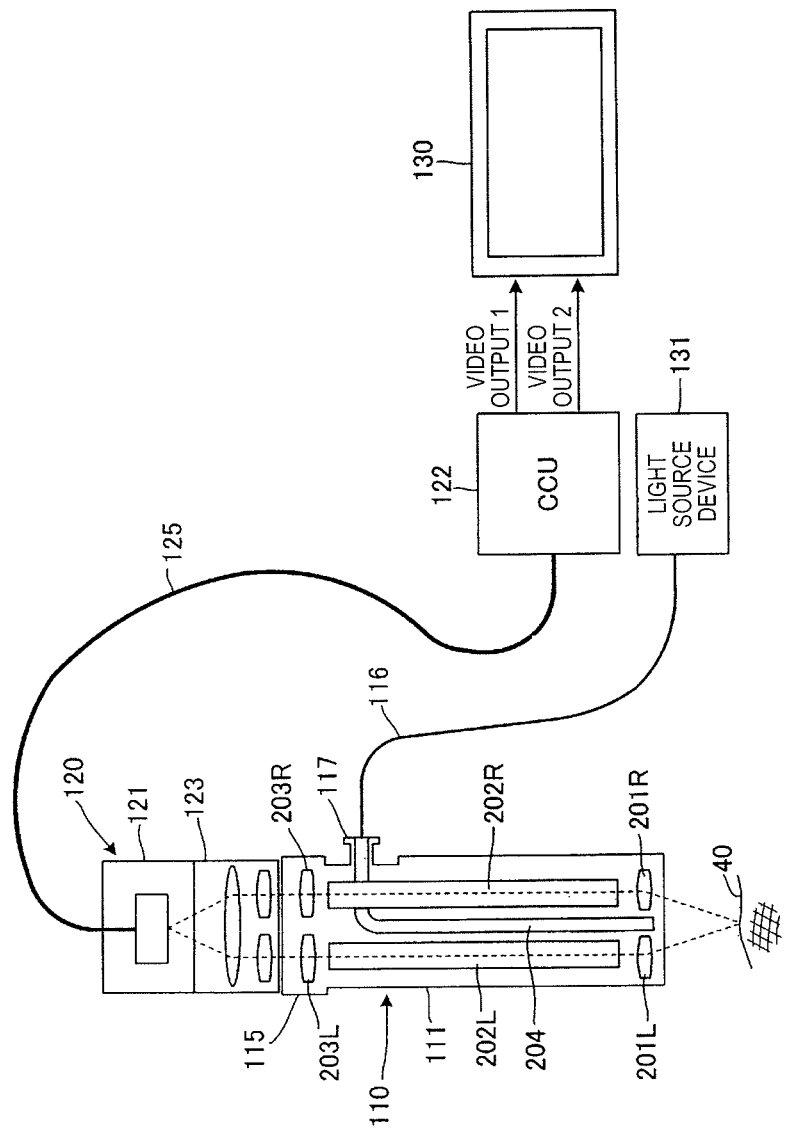
FIG. 11 is a system configuration diagram which illustrates a surgical endoscope system to which a medical camera system including the camera device according to the embodiment is applied.

FIG. 11 is a system configuration diagram which illustrates a surgical endoscope system to which a medical camera system including the camera device according to the embodiment is applied. The surgical endoscope system includes surgical endoscope 110, camera device 120, monitor 130, and light source device 131. As with camera device 20 shown in FIGS. 1 to 5, camera device 120 includes camera head 121 and CCU 122.

Surgical endoscope 110 is a stereoscopic endoscope and includes object lenses 201R and 201L, relay lenses 202R and 202L, and image forming lenses 203R and 203L as two observation optical systems which respectively correspond to right and left eyes, in long narrow insertion portion 111. Surgical endoscope 110 includes camera mounting portion 115, which is provided on the proximal side of the observation optical system, and light source mounting portion 117. Surgical endoscope 110 is provided with light guide 204 which guides illumination light from light source mounting portion 117 to a distal end portion of insertion portion 111. When image capturing is performed with image capturing lens unit 123 of camera head 121 mounted on camera mounting portion 115, observation videos for the stereoscopic observation can be obtained in camera device 120. Light guide cable 116 is connected to light source mounting portion 117 and light source device 131 is connected to light source mounting portion 117 via light guide cable 116.

Camera head 121 and CCU 122 are connected to each other via signal cable 125 and a video signal for a 3D video of the subject which is captured by camera head 121 is transmitted to CCU 122 via signal cable 125. An output terminal of CCU 122 is connected to monitor 130 and two (right and left) video outputs 1 and 2 for the 3D display operation are output thereto. The FHD resolution 3D video is displayed on monitor 130 as the observation video of the target site.

Figure 12:
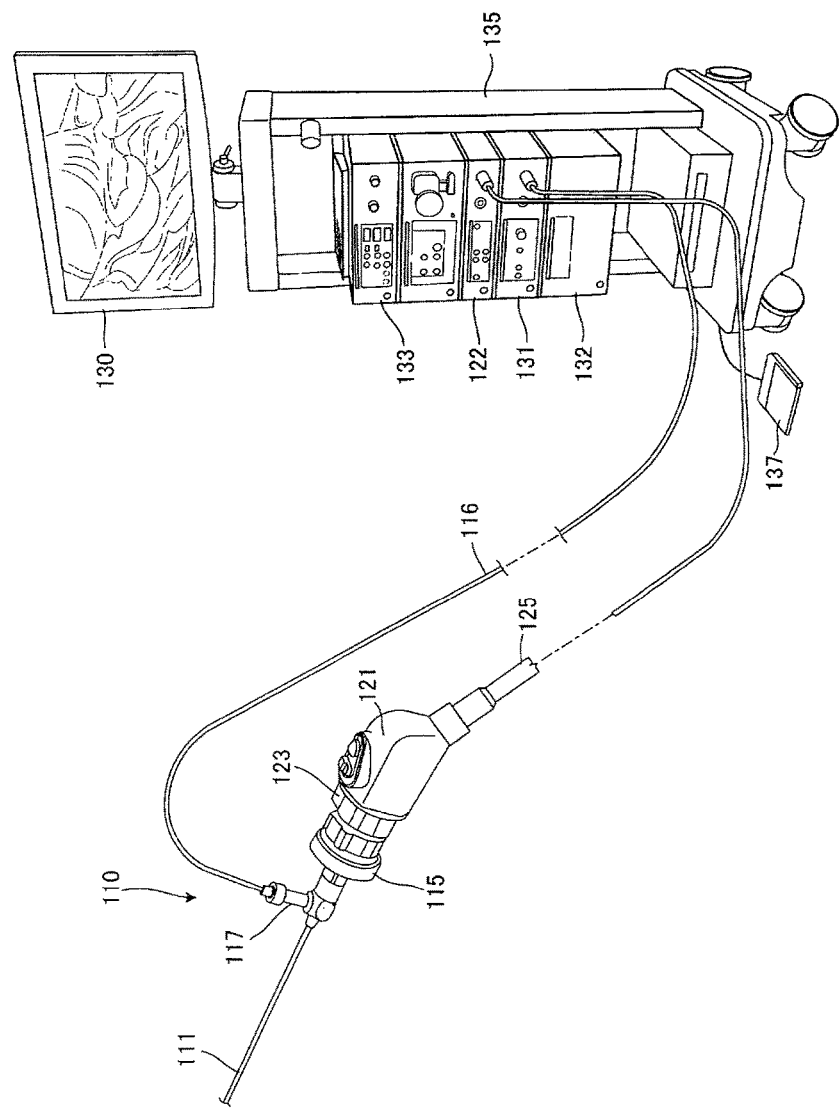
FIG. 12 is a view illustrating the appearance of the surgical endoscope system according to the embodiment.

FIG. 12 is a view illustrating the appearance of the surgical endoscope system according to the embodiment. Surgical endoscope 110 includes camera mounting portion 115 which is provided on the proximal side of insertion portion 111 and image capturing lens unit 123 of camera head 121 is mounted thereon. Light source mounting portion 117 is provided on a side portion of insertion portion 111 on the proximal side and light guide cable 116 is connected to light source mounting portion 117. Camera head 121 is provided with an operation switch and a user can performs an operation (freezing, releasing, image scanning, or the like) with respect to the captured observation video with camera head 121 on a user's hand. The surgical endoscope system includes recorder 132 which records the observation video that is captured by camera device 120, operation unit 133 for operating the surgical endoscope system, and foot switch 137 with which the observer inputs the operation by using a foot. Operation unit 133, CCU 122, light source device 131, and recorder 132 are accommodated in control unit housing 135. Monitor 130 is disposed above control unit housing 135.

As with System Configuration 1 which is described above, in System Configuration 2 of the embodiment, FHD resolution right and left parallax videos are output after being generated from right and left parallax images of the target site, which are obtained by surgical microscope 110, as described above. Therefore, the FHD resolution 3D video can be displayed on monitor 130.

In the embodiment, camera head 21 captures an FHD resolution observation video including right and left parallax videos for one screen, right and left parallax videos are cut out after a 4K video producing process in image processor 261 of CCU 22, and the FHD resolution left parallax video and the FHD resolution right parallax video for the right side and the left side are generated and output to monitor 30 as the 3D video. The 3D video is displayed on monitor 30 in such a manner that the observer can observe the left parallax video and the right parallax video with the observer's respective eyes. As a result, it is possible to capture and output the FHD resolution 3D video, of which the resolution is high, with one camera head 21 and CCU 22 and it is possible to image the target site in a stereoscopic manner at a high resolution. Accordingly, it is possible to realize space saving in the medical camera system and to realize resolution enhancement. According to the embodiment, it is possible to obtain a more clear 3D video which is particularly useful for surgery and it is possible to increase the operability in surgery and the visibility with respect to the target site.

In addition, when three-CCD image capturing unit 213 is used in camera head 21, it is possible to reduce the size of the image sensor and to increase the sensitivity of the image sensor. Accordingly, it is possible to increase the brightness of a captured video, to increase depth of field, and to reduce noise. Therefore, it is possible to obtain a video with higher image quality.

In addition, since it is possible to cope with a capturing and outputting operation of a 4K resolution 2D video and to cope with a capturing and outputting operation of an FHD resolution 3D video in one CCU 22, it is possible to cope with various uses of the observation video.

As described above, camera device 20 of the embodiment includes camera head 21 that is connected to a medical optical instrument such as surgical microscope 10 or surgical endoscope 110 and captures an observation image of a target site which is obtained by the medical optical instrument, and camera control unit (CCU) 22 that is connected to camera head 21 and processes a signal of the observation video captured by camera head 21. Camera head 21 includes image capturing unit 213 that captures right and left observation images having a parallax from the medical optical instrument to obtain a high-resolution observation video including right and left parallax videos for one screen, and CCU 22 includes image processor 261 that cuts out the right parallax video and the left parallax video from the observation video including the right and left parallax videos to generate a high-resolution 3D video which is displayed on monitor 30 in 3D and with which stereoscopic observation can be performed. Accordingly, it is possible to capture and output a high-resolution 3D video, which is required in the medical field, with one camera.

In addition, in camera device 20, image processor 261 executes any one of an operation of generating and outputting a high-resolution 2D video which is performed by inputting the high-resolution observation video captured by camera head 21 and an operation of generating and outputting a high-resolution 3D video which is performed by inputting the observation video including the right and left parallax videos in a switching manner. Accordingly, it is possible to cope with a capturing operation of a high-resolution 2D video and to cope with a capturing operation of a 3D video, and it is possible to cope with various uses of the observation video.

In addition, in camera device 20, image capturing unit 213 captures a full high vision resolution observation video including the right and left parallax videos as the high-resolution observation video, and image processor 261 performs a resolution enhancement process in which the full high vision resolution observation video is converted into a 4K resolution observation video, cuts out the left parallax video and the right parallax video from the 4K resolution observation video, and generates a 3D video from a full high vision resolution right parallax video and a full high vision resolution left parallax video. Accordingly, it is possible to cope with a capturing and outputting operation of a 4K resolution 2D video and to cope with a capturing and outputting operation of an FHD resolution 3D video, and it is possible to cope with a capturing operation of a high-resolution 3D video, which is required in the medical field, with one camera.

Although various embodiments have been described above with reference to the drawings, it is needless to say that the present disclosure is not limited to such examples. It will be apparent to those skilled in the art that various modification examples or correction examples can be conceived within the scope described in the claims, and it is needless to say that the modification examples or correction examples fall within the technical scope of the present disclosure.

The disclosure is useful for a camera device of a medical camera system that is used in, for example, a surgical microscope system, a surgical endoscope system or the like and that can capture and output a high-resolution 3D video, which is required in the medical field, with one camera.

What is claimed is:

1. A camera device which is connected to a medical optical instrument, comprising:
   a camera head that captures an observation image of a target site which is obtained by the medical optical instrument; and
   a camera controller that is connected to the camera head and processes a signal of the observation video captured by the camera head,
   wherein the camera head captures right and left observation images having a parallax from the medical optical instrument to obtain a high-resolution observation video including right and left parallax videos for one screen, and
   wherein the camera controller comprises:
   a 4K video producing unit that receives, as an input, data captured by the camera and that converts the captured input data into a 4K resolution image signal, the 4K video producing unit configured to generate and output video signals along a first route and along a second route, the second route being distinct from the first route, the video signal output along the first route being input to a 2K resolution left parallax video cutting out unit and to a 2K resolution right parallax video cutting out unit, and the video signal output along the second route comprises a 4K resolution 2-D video signal; and
   a video output switching apparatus configured to receive a 2K left parallax video signal from the left parallax video cutting out unit and a 2K right parallax video signal from the right parallax video cutting out unit along the first route and the 4K resolution 2-D video signal along the second route and to output a full high definition resolution 3-D video signal or the 4K resolution 2-D video signal,
   wherein the output of the full high definition 3-D video signal comprises the 2K left parallax video signal output as a first video output and the 2K right parallax video signal output as a second video output and,
   wherein the output of the 4K resolution 2-D video signal is output as one or both of the first video output and the second video output.

2. The camera device of claim 1,
   wherein the camera head and the camera controller are connected to each other via a cable.

3. The camera device of claim 2,
   wherein a switch that switches between outputting of the 2-D video and outputting of the 3D video is disposed on a front surface of the camera controller.

4. The camera device of claim 1,
   wherein the camera head captures a full high vision resolution observation video including right and left parallax videos as the high-resolution observation video, and
   wherein the camera controller performs a resolution enhancement process in which the full high vision resolution observation video is converted into a 4K resolution observation video, cuts out the left parallax video and the right parallax video from the 4K resolution observation video, and generates a 3-D video from a full high vision resolution right parallax video and a full high vision resolution left parallax video.

5. An image generation method using a camera device connected to a medical optical instrument, the method comprising:
   causing the camera device to capture right and left observation images having a parallax which are obtained by the medical optical instrument;

causing the camera device to obtain a high-resolution observation video including right and left parallax videos for one screen; and receiving, as an input, data captured by the camera device and converting the captured input data into a 4K resolution image signal, generating and outputting video signals along a first route and along a second route, the second route being distinct from the first route, the video signal output along the first route being input to a 2K resolution left parallax video cutting out unit and to a 2K resolution right parallax video cutting out unit, and the video signal output along the second route comprises a 4K resolution 2-D video signal; and receiving a 2K left parallax video signal from the left parallax video cutting out unit and a 2K right parallax video signal from the right parallax video cutting out unit along the first route and the 4K resolution 2-D video signal along the second route and outputting a full high definition resolution 3-D video signal or the 4K resolution 2-D video signal, wherein the outputting of the full high definition 3-D video signal comprises outputting the 2K left parallax video signal as a first video output and outputting the 2K right parallax video signal as a second video output and, wherein the outputting of the 4K resolution 2-D video signal is output as one or both of the first video output and the second video output.

6. The method of claim 5, further comprising:

causing the camera device to capture a full high vision resolution observation video including right and left parallax videos as the high-resolution observation video; and causing the camera device to perform a resolution enhancement process in which the full high vision resolution observation video is converted into a 4K resolution observation video, to cut out the left parallax video and the right parallax video from the 4K resolution observation video, and to generate a 3D video from a full high vision resolution right parallax video and a full high vision resolution left parallax video.

7. An image processor that is operatively coupled to a camera and to a display, the image processor comprising:

a 4K video producing unit that receives, as an input, data captured by the camera and that converts the captured input data into a 4K resolution image signal, the 4K video producing unit configured to generate and output video signals along a first route and along a second route, the second route being distinct from the first route, the video signal output along the first route being input to a 2K resolution left parallax video cutting out unit and to a 2K resolution right parallax video cutting out unit, and the video signal output along the second route comprises a 4K resolution 2-D video signal; and a video output switching apparatus configured to receive a 2K left parallax video signal from the left parallax video cutting out unit and a 2K right parallax video signal from the right parallax video cutting out unit along the first route and the 4K resolution 2-D video signal along the second route and to output a full high definition resolution 3-D video signal or the 4K resolution 2-D video signal, wherein the output of the full high definition 3-D video signal comprises the 2K left parallax video signal output as a first video output and the 2K right parallax video signal output as a second video output and, wherein the output of the 4K resolution 2-D video signal is output as one or both of the first video output and the second video output.

8. An image processor that is operatively coupled to a camera and to a display, the image processor comprising:

a 4K video producing unit that receives, as an input, data captured by the camera and that converts the captured input data into a 4K resolution image signal, the 4K video producing unit configured to generate and output video signals along a first route and along a second route, the second route being distinct from the first route, the video signal output along the first route being input to a 2K resolution left parallax video cutting out unit and to a 2K resolution right parallax video cutting out unit, and the video signal output along the second route comprises a 4K resolution 2-D video signal;

a video combining unit that combines a left parallax video signal output from the left parallax cutting out unit and a right parallax video signal output from the right parallax video cutting out unit and generates and outputs a high definition resolution 3-D video signal; and a video output switching apparatus configured to receive the 2K left parallax video signal from the left parallax video cutting out unit and the 2K right parallax video signal from the right parallax video cutting out unit, and the high definition resolution 3-D video signal along the first route and the 4K resolution 2-D video signal along the second route and to output a full high definition resolution 3-D video signal, the high definition resolution 3-D video signal or the 4K resolution 2-D video signal, wherein the output of the full high definition 3-D video signal comprises the left parallax video signal output as a first video output and the right parallax video signal output as a second video output, and wherein the output of the 4K resolution 2-D video signal or the high definition resolution 3-D video signal is output as one or both of the first video output and the second video output.

9. The camera device according to claim 1, wherein the controller further comprises a video combining unit that combines a left parallax video signal output from the left parallax cutting out unit and a right parallax video signal output from the right parallax video cutting out unit and generates and outputs a high definition resolution 3-D video signal.

10. The image generating method according to claim 5, further comprising combining a left parallax video signal, output from the left parallax cutting out unit, and a right parallax video signal, output from the right parallax video cutting out unit, and generating and outputting a high definition resolution 3-D video signal.

11. The image processor according to claim 7, wherein the image processor receives an image signal from the camera and outputs the full high definition resolution 3-D video signal or the 4K resolution 2-D video signal to the display.

12. The image processor according to claim 8, wherein the image processor receives an image signal from the camera and outputs the full high definition resolution 3-D video signal, the high definition resolution 3-D video signal, or the 4K resolution 2-D video signal to the display.

13. The image processor according to claim 7, wherein the 4K video processing unit receives, from the camera, 2K videos R, G, and B, and performs a resolution enhancement process by shifting pixels of 2K video R and 2K video B by one half pixel distance in a vertical direction and a horizontal direction with respect to pixels of 2K video G and generates a 4K resolution image signal.

14. The image processor according to claim 8, wherein the 4K video processing unit receives, from the camera, 2K video R, G, and B, and performs a resolution enhancement process by shifting pixels of 2K video R and 2K video B by one half pixel distance in a vertical direction and in a horizontal direction with respect to pixels of 2K video G and generates a 4K resolution image signal.

* * * * *